US012259449B2

(12) United States Patent
Xin et al.

(10) Patent No.: US 12,259,449 B2
(45) Date of Patent: Mar. 25, 2025

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventors: Yang Xin, Shanghai (CN); Suhang Mao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 135 days.

(21) Appl. No.: 18/161,302

(22) Filed: Jan. 30, 2023

(65) Prior Publication Data
US 2023/0176153 A1 Jun. 8, 2023

Related U.S. Application Data

(63) Continuation of application No. 17/004,041, filed on Aug. 27, 2020, now Pat. No. 11,567,149.

(30) Foreign Application Priority Data

Apr. 21, 2020 (CN) .......................... 202020601752.4

(51) Int. Cl.
G01R 33/28 (2006.01)
A61B 5/055 (2006.01)
G01R 33/30 (2006.01)
G01R 33/34 (2006.01)
G01R 33/385 (2006.01)
G01R 33/48 (2006.01)

(52) U.S. Cl.
CPC ............ G01R 33/283 (2013.01); A61B 5/055 (2013.01); G01R 33/307 (2013.01); G01R 33/34046 (2013.01); G01R 33/385 (2013.01); G01R 33/48 (2013.01)

(58) Field of Classification Search
CPC ............... G01R 33/283; G01R 33/307; G01R 33/34046; G01R 33/385; G01R 33/48; G01R 33/34084; G01R 33/3415; A61B 5/055; A61B 5/0033; A61B 5/0077; A61B 5/7475; G16H 20/40; G16H 30/20; G16H 30/40; G16H 40/63
See application file for complete search history.

(56) References Cited

U.S. PATENT DOCUMENTS 6,175,610 B1 * 1/2001 Peter ..................... G06F 3/011
                                                         250/221
6,684,093 B2 1/2004 Kuth
7,136,692 B2 11/2006 Graw
7,494,276 B2 2/2009 Borgmann et al.
(Continued)

Primary Examiner — G. M. A Hyder
(74) Attorney, Agent, or Firm — METIS IP LLC

(57) ABSTRACT

The present disclosure provides a system. The system may include a medical device, a couch, one or more imaging devices, and a control device. The medical device may include a cavity. The couch may be configured to support a subject. The one or more imaging devices may be configured to acquire image data. The image data may indicate at least one of a target portion of the subject or posture information of a user. The control device may be configured to control a movement of the couch based on at least one of position information of the target portion of the subject or the posture information of the user.

20 Claims, 14 Drawing Sheets

(56) References Cited

U.S. PATENT DOCUMENTS

| | | |
|---|---|---|
| 7,987,069 B2 | 7/2011 | Rodgers et al. |
| 8,018,579 B1 | 9/2011 | Krah |
| 8,390,290 B2 | 3/2013 | Sukkau |
| 8,805,476 B2 | 8/2014 | Yang |
| 8,817,085 B2 | 8/2014 | Hiltl et al. |
| 9,235,973 B2 | 1/2016 | Popescu |
| 9,375,142 B2 | 6/2016 | Schultz et al. |
| 9,569,001 B2 | 2/2017 | Mistry et al. |
| 9,652,042 B2 | 5/2017 | Wilson et al. |
| 9,710,141 B2 | 7/2017 | Braun et al. |
| 9,785,131 B2 | 10/2017 | Dirauf et al. |
| 9,943,271 B2 | 4/2018 | Dirauf et al. |
| 9,949,699 B2 | 4/2018 | Visser et al. |
| 10,098,607 B2 | 10/2018 | Grasruck et al. |
| 10,551,930 B2 | 2/2020 | Wilson et al. |
| 2002/0118280 A1 | 8/2002 | Medlar et al. |
| 2004/0081341 A1 | 4/2004 | Cherek et al. |
| 2013/0281818 A1* | 10/2013 | Vija ................... A61B 5/704 600/407 |
| 2014/0123388 A1 | 5/2014 | Filiberti |
| 2014/0155728 A1 | 6/2014 | Lee et al. |
| 2015/0320339 A1 | 11/2015 | Larson et al. |
| 2016/0113592 A1 | 4/2016 | Murugappan et al. |
| 2016/0143626 A1 | 5/2016 | Ohta et al. |
| 2016/0262663 A1 | 9/2016 | Maclaren et al. |
| 2016/0338614 A1 | 11/2016 | Gall et al. |
| 2017/0168124 A1 | 6/2017 | Ueda et al. |
| 2017/0224298 A1 | 8/2017 | Hannemann et al. |
| 2017/0311841 A1 | 11/2017 | Rothgang |
| 2017/0311842 A1 | 11/2017 | Boettger et al. |
| 2018/0014745 A1 | 1/2018 | Senegas et al. |
| 2018/0247427 A1 | 8/2018 | Geiger et al. |
| 2019/0027246 A1 | 1/2019 | Ferguson et al. |

\* cited by examiner

500

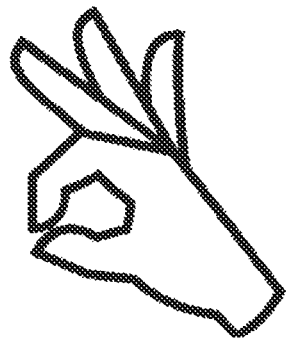
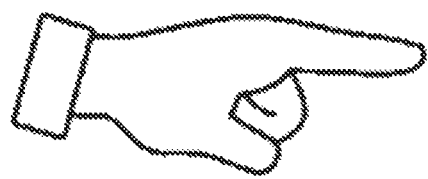
FIG. 11
FIG. 12
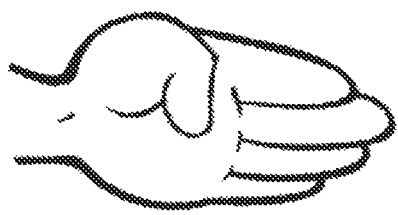
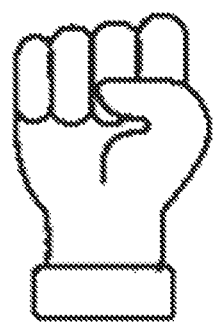
FIG. 13
FIG. 14

SYSTEMS AND METHODS FOR MAGNETIC RESONANCE IMAGING

CROSS-REFERENCE TO RELATED APPLICATIONS

This application is a continuation of U.S. application Ser. No. 17/004,041 filed on Aug. 27, 2020, which claims priority of Chinese Patent Application No. 202020601752.4, filed on Apr. 21, 2020, the contents of which are hereby incorporated by reference.

TECHNICAL FIELD

The disclosure generally relates to medical systems, and more particularly relates to systems and methods for subject positioning in a medical procedure.

BACKGROUND

A medical imaging technique, e.g., magnetic resonance imaging (MRI) is widely used for the diagnosis and/or research of an anatomical structure and/or function of a healthy body and/or a sick body. During an imaging process, a medical system (e.g., an MRI system) usually uses one or more laser lights for positioning a subject (e.g., a patient) to be scanned in a scanning region of the medical system. When the subject (e.g., a patient) enters the scanning region of the medical system, the subject (e.g., a patient) needs to be instructed to avoid the laser. After a target portion of the subject is moved to a position in the scanning region where the laser lights correspond, a scan may be performed, which may involve a risk of laser damage, and time-consuming. Therefore, it is desired to provide systems and methods for positioning a subject more efficiently and safely.

SUMMARY

According to a first aspect of the present disclosure, a system is provided. The system may include a medical device, a couch, one or more imaging devices, and a control device. The medical device may include a cavity. The couch may be configured to support a subject. The one or more imaging devices may be configured to acquire image data. The image data may indicate at least one of a target portion of the subject or posture information of a user. The control device may be configured to control a movement of the couch based on at least one of position information of the target portion of the subject or the posture information of the user.

In some embodiments, one of the one or more imaging devices may include a first end facing the couch and a second end facing away from the couch. An extension line connecting the second end with the first end may intersect a surface where a couch plate of the couch is located.

In some embodiments, one of the one or more imaging devices may include a magnetic shielding layer and a housing. The magnetic shielding layer may at least in part enclose the housing. The housing may include a housing cavity extending from the first end to the second end. The one of the one or more imaging devices may include at least one of an infrared sensor, a camera, or a video camera that is located at the first end, and the second end may be sealed.

In some embodiments, the camera may include a telephoto camera or a short-focus camera.

In some embodiments, at least one of the one or more imaging devices may be disposed at an entrance of the cavity.

In some embodiments, the system may further include one or more brackets. At least one of the one or more imaging devices may be mounted on the one or more brackets.

In some embodiments, the one or more imaging devices may include a first imaging device configured to acquire a first image including a representation of the target portion of the subject.

In some embodiments, the one or more imaging devices may include a second imaging device configured to acquire a second image including the posture information of the user.

In some embodiments, an angle between the extension line connecting the second end with the first end and the surface may be within a range of 5 degrees to 80 degrees.

In some embodiments, the medical device may further include one or more accommodating cavities configured to accommodate one or more receiving coils. The receiving coils may be capable of extending out of the one or more accommodating cavities based on the posture information of the user.

According to a second aspect of the present disclosure, a system is provided. The system may include at least one storage medium including a set of instructions, and at least one processor in communication with the at least one storage medium. When executing the set of instructions, the at least one processor may cause the system to perform one or more of the following operations. The system may obtain image data related to a subject on a couch that is acquired by one or more imaging devices when the couch is located outside a cavity of a medical device. The image data may indicate at least one of the subject or posture information of a user. The system may further determine, based on the image data, position information of the subject. The system may further cause, based at least in part on the position information of the subject, an adjustment of the position of the couch. An adjusted position of the couch may be such that the subject is moved into the cavity of the medical device.

According to a third aspect of the present disclosure, a system is provided. The system may include an MR device including a main field magnet having an examination region; a couch including a support portion and a couch plate supported by the support portion, the support portion being in communication with the MR device, the couch plate, adapted to receive a subject, being moveable relative to the support portion; one or more imaging devices configured to acquire image data, the image data indicating posture information of a user; and a control device configured to control, based on the posture information of the user, a movement of the couch plate with a target portion of the subject in order to move the target portion into the examination region.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIGS. 11-14 are schematic diagrams illustrating exemplary gestures of an operator according to some embodiments of the present disclosure;

DETAILED DESCRIPTION

Figure 1:
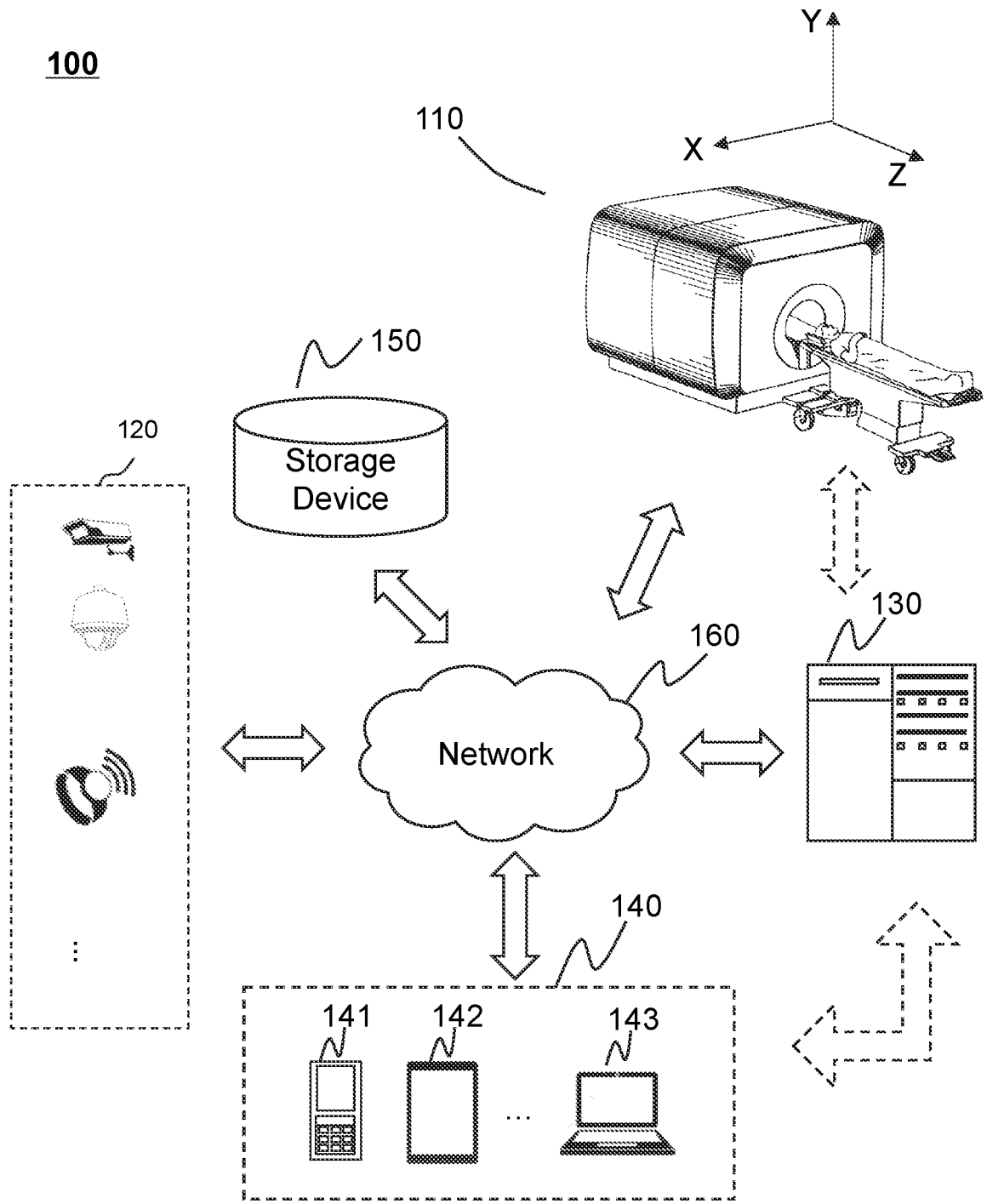
FIG. 1 is a schematic diagram illustrating an exemplary medical system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

In the present disclosure, it should be understood that the terms "center", "longitudinal", "lateral", "length", "width", "thickness", "upper", "lower", "front" "back", "left", "right", "vertical", "horizontal", "top", "bottom", "inner", "outer", "clockwise", "counterclockwise", "axial", "radial", "circumferential", etc. are indicated based on the orientation or positional relationship shown in the drawings, which are only for the convenience of describing the present disclosure and simplifying the description, not to indicate or imply that the device or element must have a specific orientation, or be constructed and operated in a specific orientation, and therefore cannot be understood as a limitation of the present disclosure.

In addition, the terms "first" and "second" are used for description purposes only, and cannot be understood as indicating or implying relative importance or implicitly indicating the number of technical features indicated. Thus, the features defined with "first" and "second" may include at least one of the features either explicitly or implicitly. In the description of the present disclosure, the meaning of "a plurality of" is at least two, such as two, three, etc., unless specifically defined otherwise.

In the present disclosure, unless otherwise clearly specified and defined, the terms "installation", "connected", "fixed", or other terms should be understood in a broad sense. For example, a connection may be a fixed connection, a detachable connection, or integrated, or may be a mechanical connection or an electrical connection, or may be directly connected, or indirectly connected through an intermediary, or may be a connection between two elements or the interaction between two elements. Unless otherwise stated, those skilled in the art can understand the specific meanings of the above terms in the present disclosure according to specific situations.

In the present disclosure, unless otherwise clearly specified and defined, the first feature "above" or "below" the second feature may be that the first and second features are in direct contact, or the first and second features are through an intermediary indirect contact. Moreover, the first feature is "above" the second feature may be that the first feature is directly above or obliquely above the second feature, or simply means that the horizontal height of the first feature is greater than that of the second feature. The first feature is "below" the second feature may be that the first feature is directly below or obliquely below the second feature, or simply means that the horizontal height of the first feature is less than that of the second feature.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Provided herein are systems and methods for performing a medical procedure (e.g., imaging and/or treatment). The system may include a medical device that includes a cavity and a couch configured to support a subject. The system may also include one or more imaging devices configured to acquire image data related to the subject on the couch. The image data may indicate at least one of a target portion of the subject or posture information of a user. The system may further include a control device configured to control a movement of the couch based on at least one of position information of the target portion of the subject or the posture information of the user. In some embodiments, the system may identify the target portion of the subject from the image data and determine the position information of the target portion based on the image data. In some embodiments, the system may identify the posture information of the user and determine the position information of the target portion based on the posture information of the user. The control device may determine a distance between the target portion of the subject and an examination region of a scanning region or treatment region of the medical device (e.g., the field of view of the medical device). The control device may cause the movement of the couch based on the distance between the target portion of the subject and the examination region of the scanning region or treatment region of the medical device. Accordingly, the target portion of a subject that needs to be imaged or treated may be automatically positioned at the examination region of a scanning region or treatment region of the medical device with improved efficiency. And without the use of one or more laser lights, the laser damage for the subject may be avoided, thereby increasing the security of the subject.

FIG. 1 is a schematic diagram illustrating an exemplary medical system 100 according to some embodiments of the present disclosure. As illustrated in FIG. 1, the medical system 100 may include a medical device 110, one or more sensing devices 120, a processing device 130, one or more terminal(s) 140, a storage device 150, and a network 160. In some embodiments, the medical device 110, the sensing devices 120, the processing device 130, the terminal(s) 140, and/or the storage device 150 may be connected to and/or communicate with each other via a wireless connection (e.g., the network 160), a wired connection, or a combination thereof. The connections between the components in the medical system 100 may vary. Merely by way of example, the sensing devices 120 may be connected to the processing device 130 through the network 160, as illustrated in FIG. 1. As another example, the storage device 150 may be connected to the processing device 130 through the network 160, as illustrated in FIG. 1, or connected to the processing device 130 directly. As a further example, the terminal(s) 140 may be connected to the processing device 130 through the network 160, as illustrated in FIG. 1, or connected to the processing device 130 directly.

The medical device 110 may include any device used in a medical procedure. As used herein, a medical procedure may refer to an activity or a series of actions attended to achieve a result in the delivery of healthcare, for example, directed at or performed on a subject (e.g., a patient) to measure, diagnosis and/or treat the subject. Exemplary medical procedures may include a diagnostic procedure (e.g., an imaging procedure), a treatment procedure (e.g., a radiotherapy treatment procedure), etc. The subject may be biological or non-biological. For example, the subject may include a patient, a man-made object, etc. As another example, the subject may include a specific portion, organ, and/or tissue of the patient. For example, the subject may include the head, the neck, the thorax, the heart, the stomach, blood vessels, soft tissues, tumors, nodules, or the like, or a combination thereof.

In some embodiments, the medical device 110 may include an imaging device, a treatment device (e.g., a radiotherapy equipment), a multi-modality device to acquire one or more images of different modalities or acquire an image relating to at least one part of a subject and perform treatment on the at least one part of the subject, etc. The imaging device may be configured to generate an image including a representation of at least one part of the subject. Exemplary imaging devices may include, for example, a computed tomography (CT) device, a cone beam CT device, a positron emission computed tomography (PET) device, a volume CT device, a magnetic resonance imaging (MRI) device, or the like, or a combination thereof. The treatment device may be configured to perform a treatment on at least one part of the subject. Exemplary treatment devices may include a radiotherapy device (e.g., a linear accelerator), an X-ray treatment device, etc.

The sensing devices 120 may be configured to sense the environment around the sensing devices 120 and/or itself state. In some embodiments, the sensing devices 120 may include one or more sensors. The one or more sensors may include an image sensor, a localization sensor (e.g., a GPS receiver), a distance sensor (e.g., LIADR), an infrared sensor, etc.

The image sensor may also be referred to as a visual sensor or an imaging device, etc. The visual sensor may refer to an apparatus for visual recording. In some embodiments, the imaging device may include a stereo camera configured to capture a static image or video. The stereo camera may include a binocular vision device or a multi-camera. In some embodiments, the visual sensors may include a digital camera. The digital camera may include a 2D camera, a 3D camera, a panoramic camera, a VR (virtual reality) camera, a web camera, an instant picture camera, an infrared (IR) camera, an RGB sensor, an RGBD camera, a near-infrared (NIR) sensor, a far-infrared (FIR) sensor, a range sensor, or the like, or any combination thereof.

The image sensor may be configured to obtain image data relating to one or more scenes associated with the medical device 110. The image data may include a static image, a video, an image sequence including multiple static images, etc. For example, the image data may include a representation of at least a portion of the medical device 110. As another example, the image data may include a representation of a subject on a couch to be scanned or treated. As still another example, the image data may include a representation of an operator of the medical device 110. In some embodiments, the sensing devices 120 may transmit the collected image data to the processing device 130, the storage device 150, and/or the terminal(s) 140 via the network 160. More descriptions for the sensing devices 120 may be found elsewhere in the present disclosure (e.g., FIGS. 5-10, and the descriptions thereof).

The processing device 130 may process data and/or information obtained from the medical device 110, the sensing devices 120, the terminal(s) 140, and/or the storage device 150. In some embodiments, the processing device 130 may obtain image data related to a subject on a couch that is acquired by the sensing devices 120 when the couch is at a position. The processing device 130 may determine, based on the image data, the target portion of the subject and determine, based on the image data, position information of the target portion of the subject. The processing device 130 may cause, based at least in part on the position information of the target portion, an adjustment of the position of the couch. The adjusted position of the couch may be such that the target portion of the subject is located at an examination region of a cavity of a medical device. In some embodiments, the processing device 130 may cause the medical device to perform a medical procedure on the subject. In some embodiments, the processing device 130 may determine, based on image data acquired by the sensing devices 120, posture information of an operator. The processing device 130 may control the movement of the couch based on the posture information of the operator.

In some embodiments, the processing device 130 may be a single server or a server group. The server group may be centralized or distributed. In some embodiments, the processing device 130 may be local or remote. For example, the processing device 130 may access information and/or data from the medical device 110, the terminal(s) 140, the storage device 150, and/or the sensing devices 120 via the network 160. As another example, the processing device 130 may be directly connected to the medical device 110, the sensing devices 120, the terminal(s) 140, and/or the storage device 150 to access information and/or data. In some embodiments, the processing device 130 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 130 may be implemented by a mobile device 300 having one or more components as described in connection with FIG. 3.

The terminal(s) 140 may be connected to and/or communicate with the medical device 110, the processing device 130, the storage device 150, and/or the sensing devices 120. For example, the terminal(s) 140 may obtain a processed image from the processing device 130. As another example, the terminal(s) 140 may obtain image data acquired via the sensing devices 120 and transmit the image data to the processing device 130 to be processed. In some embodiments, the terminal(s) 140 may include a mobile device 141, a tablet computer 142, . . . , a laptop computer 143, or the like, or any combination thereof. For example, the mobile device 141 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to the processing device 130 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 130.

The storage device 150 may store data, instructions, and/or any other information. In some embodiments, the storage device 150 may store data obtained from the medical device 110, the terminal(s) 140, the processing device 130, and/or the sensing devices 120. In some embodiments, the storage device 150 may store data and/or instructions that the processing device 130 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 160 to communicate with one or more other components in the medical system 100 (e.g., the processing device 130, the terminal(s) 140, the visual sensor, etc.). One or more components in the medical system 100 may access the data or instructions stored in the storage device 150 via the network 160. In some embodiments, the storage device 150 may be part of the processing device 130.

The network 160 may include any suitable network that can facilitate the exchange of information and/or data for the medical system 100. In some embodiments, one or more components of the medical system 100 (e.g., the medical device 110, the terminal(s) 140, the processing device 130, the storage device 150, the sensing devices 120, etc.) may communicate information and/or data with one or more other components of the medical system 100 via the network 160. For example, the processing device 130 may obtain image data from the visual sensor via the network 160. As another example, the processing device 130 may obtain user instruction(s) from the terminal(s) 140 via the network 160. The network 160 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, switches, server computers, and/or any combination thereof. For example, the network 160 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 160 may include one or more network access points. For example, the network 160 may include wired and/or wireless network access points such as base stations and/or internet exchange points through which one or more components of the medical system 100 may be connected to the network 160 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as public cloud, private cloud, community, and hybrid clouds, etc. However, those variations and modifications do not depart the scope of the present disclosure.

Figure 2:
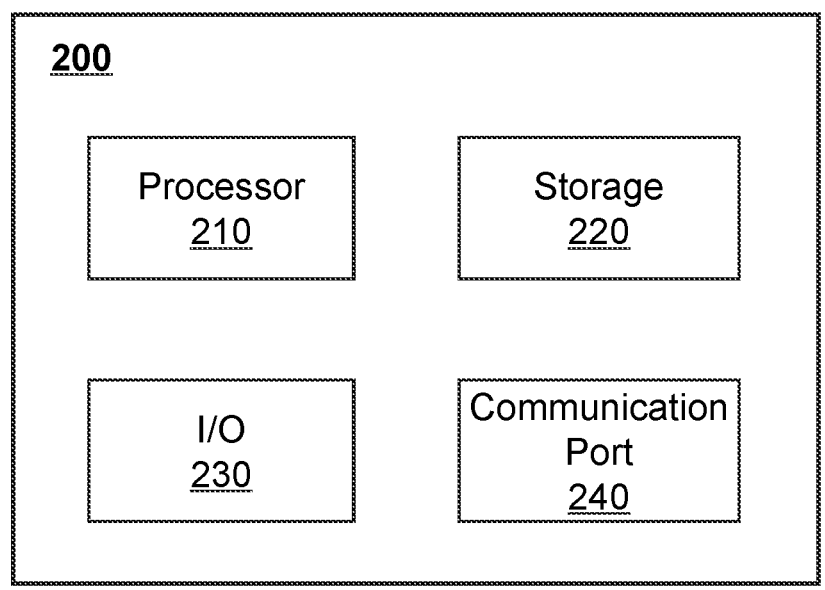
FIG. 2 is a schematic diagram illustrating hardware and/or software components of an exemplary computing device according to some embodiments of the present disclosure.

FIG. 2 is a schematic diagram illustrating hardware and/or software components of an exemplary computing device 200 on which the processing device 130 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program codes) and perform functions of the processing device 130 in accordance with techniques described herein. The computer instructions may include, for example, routines, programs, objects, components, signals, data structures, procedures, modules, and functions, which perform particular functions described herein. For example, the processor 210 may cause an adjustment of the position of a couch based on image data acquired by the sensing devices 120 in a medical procedure. The adjusted position of the couch may be such that the target portion of the subject is located at an examination region of a cavity of the medical device. As another example, the processor 210 may cause the medical device to perform the medical procedure on the subject when the couch is located at the adjusted position. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal(s) 140, the storage device 150, or any other component of the medical system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 130 to perform an imaging scan on the subject.

The I/O 230 may input or output signals, data, and/or information. In some embodiments, the I/O 230 may enable user interaction with the processing device 130. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 160) to facilitate data communications. The communication port 240 may establish connections between the processing device 130 and the medical device 110, the terminal(s) 140, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
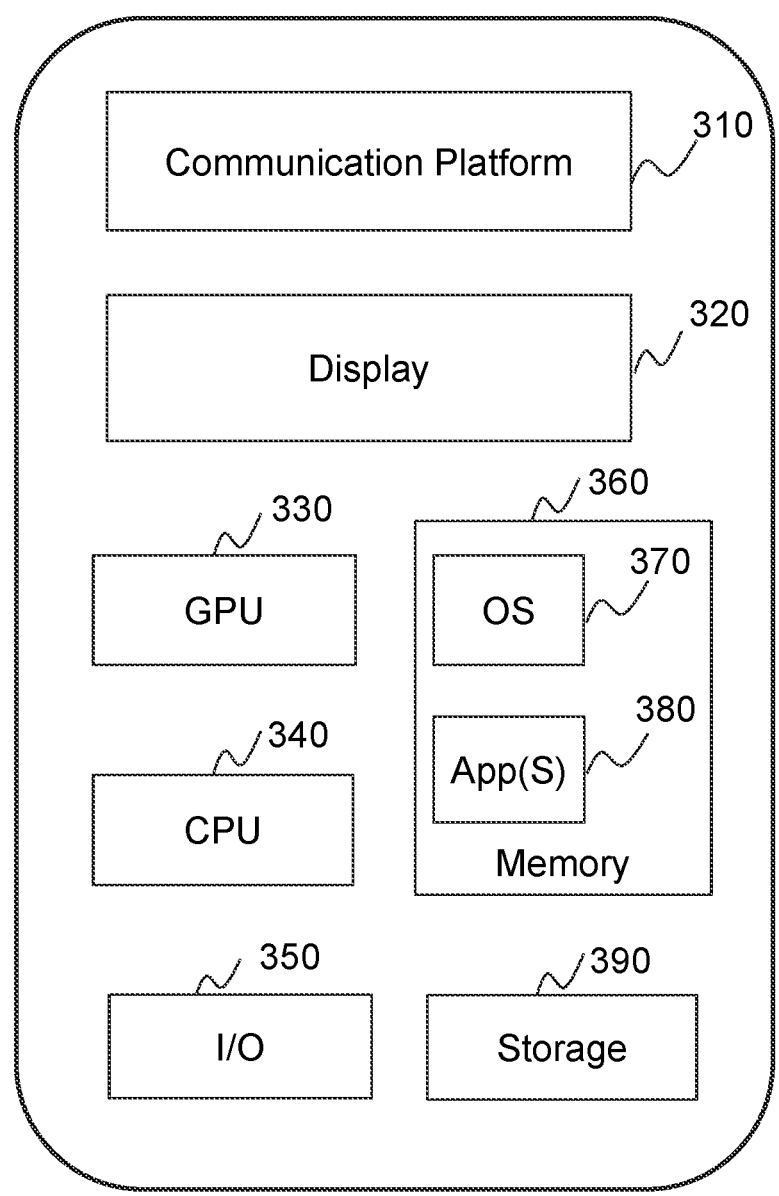
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 130. User interactions with the information stream may be achieved via the I/O 350 and provided to the processing device 130 and/or other components of the medical system 100 via the network 160.

To implement various modules, units, and functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
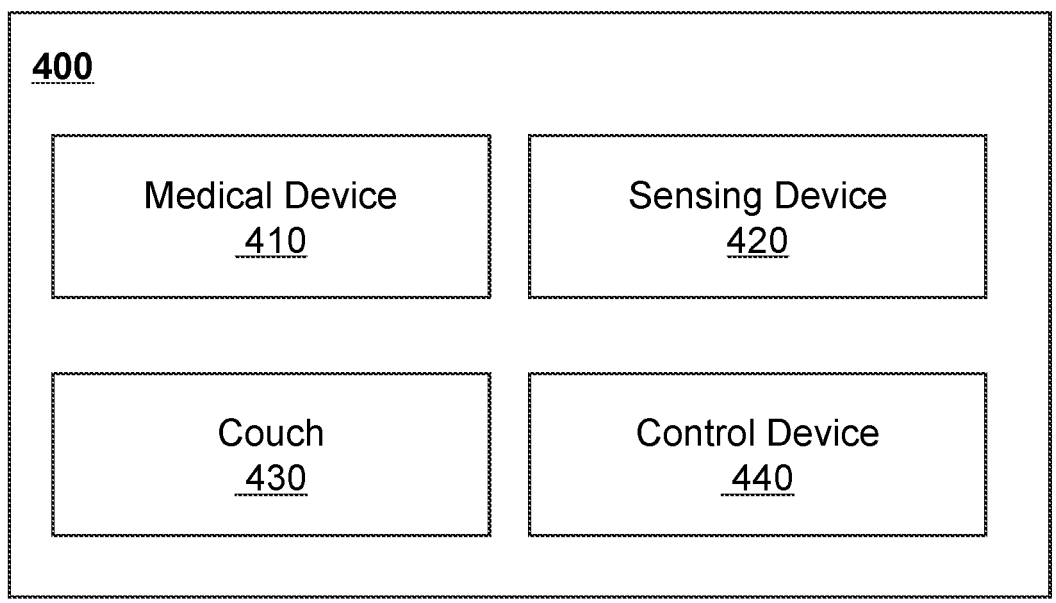
FIG. 4 is a block diagram illustrating an exemplary medical apparatus according to some embodiments of the present disclosure.

FIG. 4 is a block diagram illustrating an exemplary medical apparatus according to some embodiments of the present disclosure. In some embodiments, the medical apparatus 400 may include a medical device 410, one or more sensing devices 420, a couch 430, and a control device 440.

The medical device 410 may include any device used in a medical procedure (e.g., an imaging procedure, a treatment procedure, etc.). In some embodiments, the medical device 410 may include an imaging device, a treatment device (e.g., a radiotherapy equipment), a multi-modality device to acquire one or more images of different modalities or acquire an image relating to at least one part of a subject and perform treatment on the at least one part of the subject, etc., as described elsewhere in the present disclosure (e.g., FIG. 1, and the descriptions thereof). For example, the medical device 410 may include an MRI scanner, a CT scanner, a PET scanner, etc.

In some embodiments, the medical device 410 may include a cavity. The cavity may be configured to accommodate a subject to be imaged or treated. The cavity may include a scanning region or a treatment region of the medical device 410. The subject may be biological or non-biological. For example, the subject may include a patient, a man-made object, etc. As another example, the subject may include a specific portion, organ, and/or tissue of the patient. For example, the subject may include the head, a hand, the neck, the thorax, the heart, the stomach, a blood vessel, soft tissue, a tumor, nodules, an arm, a leg, the pelvic cavity, or the like, or any combination thereof. In some embodiments, the shape of the cross section of the cavity may be circular, rectangular, oval, triangular, or the like.

In some embodiments, the one or more sensing devices 420 may include one or more imaging devices. The one or more imaging devices may be configured to acquire image data relating to a scene associated with a medical procedure. For example, the one or more imaging devices may acquire image data including a representation of at least one part of the subject who receives the medical procedure (e.g., imaging or treatment). As another example, the one or more imaging devices may acquire image data including a representation of at least a portion of an operator who operates the medical device to perform the medical procedure. As a further example, the image data acquired by the one or more imaging devices may indicate at least one of a target portion (e.g., the head, the abdomen, the leg, etc.) of the subject or posture information of the operator. The posture information of the operator may include one or more actions of at least a portion of the body of the operator. For example, at least a portion of the body of the operator may include a hand, the head, a leg, etc. The one or more postures of at least a portion of the body of the operator may include an action of a hand (i.e., gesture), an action of the head (e.g., nod, raising the head, shaking the head, etc.), etc.

The image data may include one or more discrete images, a video, point cloud data, or the like, or a combination thereof. The image data may be a two-dimensional (2D) imaging data, a three-dimensional (3D) imaging data, a four-dimensional (4D) imaging data, or the like, or any combination thereof.

In some embodiments, the one or more imaging devices may be located outside the cavity of the medical device 410. For example, the one or more imaging devices may be mounted on the ceiling or a wall of the room where the medical device 410 is located. As another example, the one or more one or more imaging devices may be mounted on the medical device 410 and located at the entrance of the cavity.

In some embodiments, the one or more sensing devices 420 may include a distance sensor configured to detect a distance between the distance sensor and the operator, a distance between the couch 430 to a reference subject (e.g., the operator, the medical device 410, etc.), a movement distance of the couch 430, etc. The distance sensor may include an ultrasonic ranging sensor, a laser ranging sensor, an infrared ranging sensor, a radar sensor, etc. In some embodiments, the distance sensor may be mounted on the couch 430. In some embodiments, the distance sensor may be mounted on the medical device 410.

In some embodiments, the one or more sensing devices 420 may include an infrared sensor. In some embodiments, the infrared sensor may generate an infrared ray and/or sense an infrared lay radiated by an object (e.g., the subject, the operator, etc.). The infrared sensor may include a photon detector, a thermal detector, etc. In some embodiments, the infrared sensor may be mounted on the medical device 410. The infrared sensor may be mounted on the ceiling or a wall of the room where the medical device 410 is located.

The couch 430 may be configured to support the subject and/or carry the subject in or out of the cavity. In some embodiments, the couch 430 may include a support portion and a couch plate supported by the support portion. The support portion may be fixed or mobile. For example, the support portion may be fixedly connected to the medical device 410 or the ground. The couch plate may be moveable relative to the support portion. As another example, the support portion may include one or more slidable wheels at the lower end of the support portion.

The control device 440 may be configured to control the operation of one or more components of the medical apparatus 400. For example, the control device may control the movement of the couch 430. As another example, the control device may control the operation of the one or more sensing devices 420 and/or the medical device 410. In some embodiments, the control device 440 may be integrated into the medical device 410. In some embodiments, the control device 440 may be separated from the medical device 410. In some embodiments, the control device 440 may be integrated into a terminal (e.g., the terminal(s) 140).

In some embodiments, the control device 440 may include a processing engine (e.g., the processing device 130 as described in FIG. 1 (e.g., a single chip microcomputer)). The processing engine may process data and/or information obtained from the medical device 410, the sensing devices 420, and/or a storage device to control the operation of the one or more components of the medical apparatus 400. For example, the processing engine may determine a target portion (e.g., a region of interest) of a subject to be scanned or treated based on image data acquired by the one or more sensing devices (e.g., the first imaging device 524) when the couch 430 at a first location before the subject is scanned or treated. The processing engine may determine position information of the target portion of the subject. The processing engine may cause the couch 430 to move to a second position such that the target portion of the subject may be moved at an examination region of the cavity of the medical device. In some embodiments, the examination region of the cavity of the medical device may refer to a center of a main field magnet.

As a further example, the processing engine may determine a location of the target portion of the subject with respect to a reference location (e.g., an end of the couch 530) that are represented in the image data of the subject. The processing engine may determine a distance between the reference location and the examination region of the cavity. The processing engine may determine a distance that the couch needs to move based on the distance between the reference location and the examination region of the cavity and the location of the target portion of the subject with respect to the reference location. More descriptions for controlling the movement of the couch based on image data may be found elsewhere in the present disclosure (e.g., FIG. 17).

In some embodiments, the control device 440 may control the movement of the couch 430 based on the posture information of an operator of the medical procedure. For example, the processing engine may identify the action of a type from the image data acquired by the one or more sensing device 420. The action of a type may indicate a control instruction of the couch 430. The control instruction of the couch 430 may be used to control the movement direction, the movement speed, the movement distance, etc., of the couch 430. For example, the control instruction may include "stop," "move forward," "move backward," "rise," "drop," "move forward with 5 centimeters," etc. Each type of action may correspond to a control instruction of the couch 430. The processing engine may determine the control instruction of the couch 430 based on the action of a type identified from the image data and cause the operation of the couch 430 based on the control instruction. More descriptions for the action of a type may be found elsewhere in the present disclosure (e.g., FIGS. 11-14 and the descriptions thereof).

In some embodiments, the control device 440 may control the movement of the couch 430 based on a distance between the one or more sensing devices 420 (e.g., the distance sensor) and the operator. For example, the processing engine may determine a control instruction based on the distance between the one or more sensing devices 520 (e.g., the distance sensor) and the operator. Different distances may correspond to different control instructions. For example, a first distance (e.g., 0.5 meters) between the one or more sensing devices 420 (e.g., the distance sensor) and the operator may correspond to "move forward" or "move forward with 0.5 meters." A second distance (e.g., 1 meter) between the one or more sensing devices 420 (e.g., the distance sensor) and the operator may correspond to "move backward" or "move backward with 0.5 meters." The operator may change the distance with the one or more sensing devices 420 to control the movement of the couch 430. In some embodiments, the distance sensor may transmit the distance between the one or more sensing devices 420 (e.g., the distance sensor) and the operator to a terminal associated with the operator in real-time and the operator may change the distance with the one or more sensing devices 420 (e.g., the distance sensor) until the distance with one or more sensing devices 420 (e.g., the distance sensor) meets a requirement. In some embodiments, the processing engine may receive an input of the operator indicating an operation for confirming the distance between the one or more sensing devices 420 (e.g., the distance sensor) and the operator if the distance between one or more sensing devices 420 (e.g., the distance sensor) and the operator meets a requirement. For example, the operator may generate the input via the terminal. As another example, the operator may generate the input via the posture information (e.g., a hand gesture (e.g., the "OK" gesture or a "victory" posture).

In some embodiments, the control device may control the movement of the couch 430 based on a location where the operator blocks an infrared light emitted by the infrared sensor. For example, the processing engine may determine a control instruction based on the location where the operator blocks the infrared light emitted by the infrared sensor. Different locations where the operator blocks the infrared light may correspond to different control instructions. For example, if the operator blocks the infrared light emitted by the infrared sensor at a first location, the control device may cause the couch 430 to move along a first direction (e.g., "move forward"); if the operator blocks the infrared light emitted by the infrared sensor at a second location, the control device may cause the couch 430 to move along a second direction (e.g., "move backward"); if the operator blocks the infrared light emitted by the infrared sensor at a third location that is different from the first location and the second location, the control device may cause the couch 430 to stop moving.

In some embodiments, the control device may be in communication with or connected to the one or more sensing devices 420 via a wireless connection (e.g., Bluetooth, WIFI), a wired connection, or a combination thereof as described elsewhere in the present disclosure (e.g., FIG. 1 and the descriptions thereof).

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure.

Figure 5:
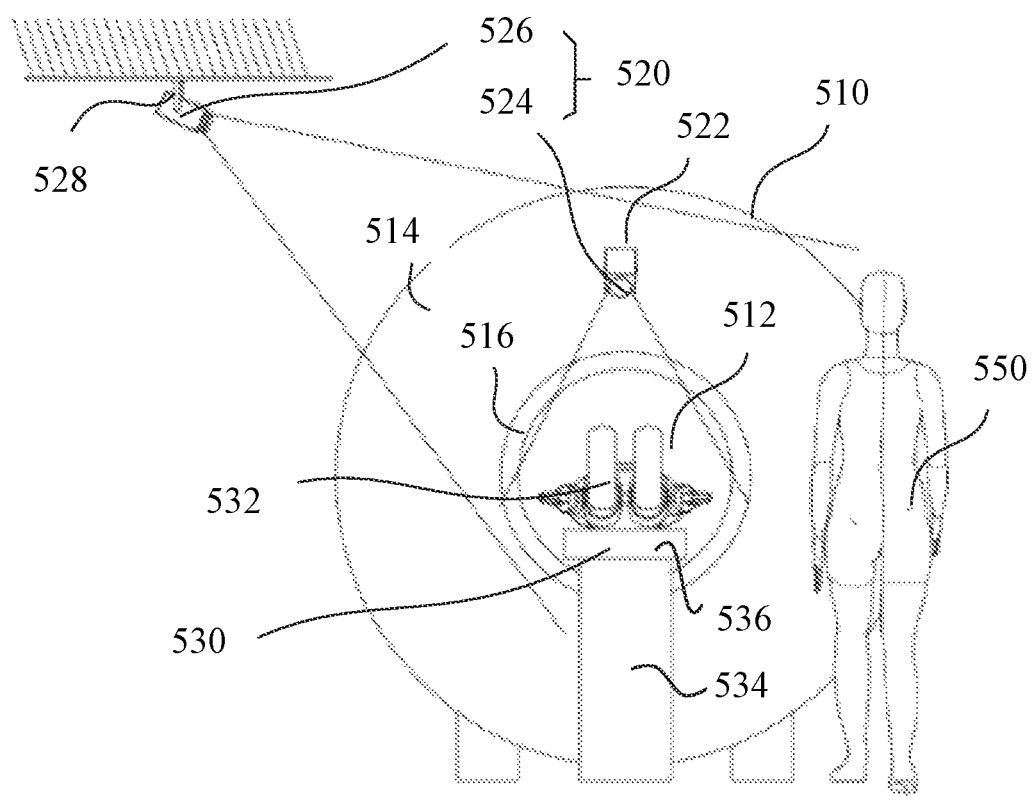
FIG. 5 is a schematic diagram illustrating a side view of an exemplary medical system according to some embodiments of the present disclosure.

FIG. 5 is a schematic diagram illustrating a side view of an exemplary medical system according to some embodiments of the present disclosure. As shown in FIG. 5, the medical system 500 may include a medical device 510, one or more imaging devices 520, and a couch 530.

The medical device 510 may include any device used in a medical procedure (e.g., an imaging procedure, a treatment procedure, etc.). More descriptions for the medical device as described elsewhere in the present disclosure (e.g., FIGS. 1 and 4, and the descriptions thereof). For example, the medical device 510 may include an MR device. The MR device may generate MR signals (e.g., echoes) of a subject (e.g., a subject 532 as shown in FIG. 5) after the subject is excited by radiofrequency (RF) transmitting pulses in a magnetic field based on the characteristics of nuclear spin motion. The MR device may detect the MR signals and transmit the MR signals into a computing device (e.g., the processing device 130 as described in FIG. 1). The computing device may process the MR signals and generate an MR image of the subject. The MR image of the subject may be presented on a display device (e.g., a display screen) of a terminal (e.g., the terminals(s) 140). The MR device may include a main body (e.g., a gantry), a magnetic assembly, a coil assembly, or the like, or a combination thereof that are located in the main body. The magnetic unit may mainly include a main magnet configured to generate a strong main magnetic field B0. The coil assembly may include a gradient coil that is configured to a gradient magnetic field and a volume coil that is configured to generate RF transmitting pulses.

In some embodiments, the medical device 510 may include a cavity 512 and an entrance 516. The medical device 510 may further include an entrance surface 514 where the entrance 516 is located. The cavity 512 may be configured to accommodate the subject 532. In some embodiments, the shape of the cross section of the cavity 512 may be circular, rectangular, oval, triangular, or the like. The subject 532 may be moved in or out the cavity 512 through the entrance 516.

The couch 530 may be configured to support the subject 532 and carry the subject 532 in or out of the cavity 512. In some embodiments, the couch 530 may include a support portion 534 and a couch plate 536 supported by the support portion 534. The support portion 534 may be fixed or mobile. For example, the support portion may be fixedly connected to the medical device 510 or the ground. The couch plate 536 may move relative to the support portion 524 to carry the subject 532 in or out of the cavity 512. As another example, the support portion 534 may include one or more slidable wheels at the lower end of the support portion. In some embodiments, the support portion 534 may include a power socket, an optical fiber socket, a cable socket, or the like, or any combination thereof. The power socket may be configured to realize the instantaneous on or off of the power. The optical fiber socket or the cable socket may be configured to realize the communication (e.g., signal transmission) between the couch 530 and the medical device 510. In some embodiments, the couch 530 and the medical device 510 may be in communication (e.g., signal transmission) via a wireless connection such as WiFi, Bluetooth, NFC, or the like.

The one or more imaging devices 520 may be configured to acquire image data relating to a scene associated with the medical device 510. For example, the imaging devices 520 may acquire image data including a representation of at least one part of the subject 532. As another example, the imaging devices 520 may acquire image data including a representation of at least a portion of a user 550. As a further example, the image data acquired by the one or more imaging devices 520 may indicate at least one of a target portion (e.g., the head, the abdomen, the leg, etc.) of the subject 532 or posture information of a user 550. The posture information of the user 550 may include one or more actions of at least a portion of the body of the user 550. For example, at least a portion of the body of the user 550 may include a hand, the head, a leg, etc. The one or more actions of at least a portion of the body of the user 550 may include an action of a hand (i.e., gesture), an action of the head (e.g., nod, raising the head, shaking the head, etc.).

In some embodiments, the imaging devices 520 may include one single imaging device, for example, a first imaging device 524 or a second imaging device 526. In some embodiments, the first imaging device 524 may include a video camera or a camera. The first imaging device 524 may be configured to acquire image data of the user 550 and/or the subject 532. For example, the first imaging device 524 may acquire the posture information of the user 550. As another example, the first imaging device 524 may acquire an image of the subject 532 before the subject 532 is moved into the cavity 512. In some embodiments, the first imaging device 524 may acquire the image data in real-time, or at an appropriate time according to user requirements. For example, the user 550 may control the first imaging device 524 to operate via a terminal when a medical procedure is performed. When the user 550 needs to change the location of the couch 530, the user 550 may make a specific gesture or action that may be captured by the first imaging device 524. The first imaging device 524 may acquire a corresponding image or video, and send the image or video with the posture information to a control device or a processing device (e.g., the processing device 130 as shown in FIG. 1). The control device may perform a recognition operation on the image or video to determine the specific gesture or action (i.e., posture information). When the specific gesture or action is recognized, the control device may correspondingly control the movement of the couch 530 based on the recognized gesture or action.

In some embodiments, the field of view of the first imaging device 524 may cover the movement region of the user 550 and/or the couch 530. In some embodiments, an angle between a line connecting the first imaging device 524 and the couch 530 (e.g., an end of the couch 530) and a horizontal line or the surface where the couch plate 536 of the couch 530 is located may be within a range of 5 degrees to 80 degrees, or a range of 40 degrees to 50 degrees, or equal to 45 degrees, etc. In other words, the first imaging device 524 may be located at a position that has an angle with the couch 530 in a range of 5 degrees to 80 degrees, or in a range of 40 degrees to 50 degrees, or being of 45 degrees, etc.

In some embodiments, the first imaging device 524 may be mounted on the medical device 510 and located outside the cavity 512. For example, the first imaging device 524 may be mounted on the entrance surface 514 at the entrance 516 of the cavity 512. The entrance 516 may be disposed at one end of the medical device 510. The other end of the medical device 510 may be sealed. The entrance surface 514 may be an end surface where the entrance 516 is located. The first imaging device 524 may be fixedly disposed on the top of the entrance surface 514, or may be movably disposed on the entrance surface 514. Since the user 550 generally stands near the entrance 516 when the user 550 operates the medical device 510 or controls the couch 530 to move in or out the cavity 512, the first imaging device 524 being located at the entrance 516 of the medical device 510 may facilitate the acquisition of the posture information of the user 550. Especially, the first imaging device 524 being disposed on the top of the entrance surface 514 may have a larger field of view, thereby acquiring posture information of the user 550 and/or image data of the subject 532 more accurately.

In some embodiments, the first imaging device 524 may be disposed on the ceiling or wall of the scanning room where the medical system 100 is placed, and the first imaging device 524 may be fixed or rotated on a side of the couch 530. An angle between a line connecting the first imaging device 524 and the couch 530 and a horizontal line or the surface where the couch plate 536 is located may be within a range of 5 degrees to 80 degrees. The first imaging device 524 being mounted on the ceiling of the scanning room may form a larger field of view and avoid being blocked by other components.

In some embodiments, the first imaging device 524 may be fixedly or rotatably mounted on a first bracket 522. In some embodiments, the first bracket 522 may have a triangular structure that includes three fixed points. Two fixed points of the triangular structure may be used to mount the first bracket 522 on the entrance surface 514 or other structures (e.g., the wall or ceiling). The third fixed point of the triangular structure may be configured to fix the first imaging device 524 on the first bracket 522. When the first imaging device 524 is disposed on the entrance surface 514 via the first bracket 522, the first imaging device 524 may be mounted on the first bracket 522, and the first bracket 522 may be fixed on the entrance surface 514 or other structures (e.g., the wall or ceiling), which is convenient and fast for mounting or dismantle the first imaging device 524. In some embodiments, the first imaging device 524 may be rotatably mounted on the first bracket 522. For example, the first imaging device 524 may be mounted on the first bracket 522 through a rotating shaft. The first imaging device 524 may rotate via the rotating shaft. The rotation of the first imaging device 524 on the first bracket 522 may expand the field of view of the first imaging device 524.

In some embodiments, the imaging devices 520 may include multiple imaging devices. For example, the imaging devices 520 may include the first imaging device 524 and the second imaging device 526. The second imaging device 526 may include a camera or a video camera. In some embodiments, the first imaging device 524 may acquire image data of the user 550, and the second imaging device 526 may acquire image data of the subject 532 on the couch 530. In some embodiments, the second imaging device 526 may acquire image data of the subject 532 and/or the image data of the user 550.

In some embodiments, the second imaging device 526 may be disposed at the entrance 516. If the first imaging device 524 is disposed at the entrance 516, the second imaging device 526 may be spaced apart from the first imaging device 524. In some embodiments, the second imaging device 526 may be disposed around the entrance 516. The specific position of the second imaging device 526 may not be limited, as long as the second imaging device 526 can acquire the image data of the subject 532. In some embodiments, the second imaging device 526 may be disposed on the medical device 510. For example, the second imaging device 526 may be disposed on the entrance surface 514. In some embodiments, the second imaging device 526 may be disposed in the room (e.g., the wall or ceiling of the room) where the medical system 100 is located.

In some embodiments, the second imaging device 526 may be disposed above the couch 530 (e.g., the ceiling of the room above the couch 530) and the first imaging device 524 may be disposed directly above the entrance surface 514. In some embodiments, an angle between a line connecting the second imaging device 526 and the couch 530 (e.g., an end of the couch 530) and a horizontal line or a surface where the couch plate 536 of the couch 530 is located may be within a range of 5 degrees to 80 degrees or equal to 45 degrees. Accordingly, the second imaging device 526 may have a larger field of view and have no interference with the first imaging device 524, which is convenient to collect images of the subject 532.

In some embodiments, the medical system 100 may include a second bracket 528. The second imaging device 526 may be rotatably mounted or fixedly mounted on the second bracket 528. The second bracket 528 may be mounted on the wall of the room where the medical system 100 is located, which may facilitate the adjustment of the position of the second imaging device 526. The structure of the second bracket 528 may be the same as or similar to that of the first bracket 522.

In some embodiments, the medical system 500 may include a control device (not shown). The control device may be configured to control the movement of the couch 530. In some embodiments, the control device may include a processing engine (e.g., the processing device 130 as described in FIG. 1 (e.g., a single chip microcomputer)). The processing engine may identify the target portion (e.g., a region of interest) of the subject 532 based on image data acquired by the one or more imaging devices 520 (e.g., the first imaging device 524) when the couch 530 at a first location when the subject 532 is at the outside of the cavity 512. The processing engine may determine position information of the target portion of the subject 532 based on the image data. The processing engine may cause the couch 530 to move at a second position such that the target portion of the subject 532 may be moved at a center position of the cavity 512. More descriptions for control the movement of the couch based on image data may be found elsewhere in the present disclosure (e.g., FIG. 17).

In some embodiments, the first imaging device 524 may acquire image data of the user 550, and the second imaging device 526 may acquire image data of the subject 532 on the couch 530. The coordinate transform relationship between the first imaging device 524 and the second imaging device 526 may be known, or the first imaging device 524 and the second imaging device 526 may share the same coordinate system, or the coordinate systems of the first imaging device 524 and the second imaging device 526 may be orthogonal. In some embodiments, the position that the user 550's gesture is located may represent the target portion of the subject 532 and may be determined from the image data acquired by the first imaging device 524. According to the coordinate transform relationship between the first imaging device 524 and the second imaging device 526, the processing engine may determine the position of the target portion of the subject 532 in the image data acquired by the second imaging device 526 based on the position where the user 550's gesture is located in the image data acquired by the first imaging device 524.

In some embodiments, one or more receiving coils may be placed on the surface of the subject 532, and a positioning marker may be provided on each of the receiving coils. An image obtained by the second imaging device 526 may include the positioning marks of the receiving coils 615. The processing engine may determine a positioning mark represented in an image collected by the second imaging device 526 with the shortest distance to the gesture represented in an image collected by the first imaging device 524, and a region corresponding to the determined positioning mark may represent the target portion to be scanned.

In some embodiments, after the subject 532 is moved into the cavity 512 by the couch 530, the control device may perform a secondary position adjustment. The control device may control the medical device 510 to obtain an overview image (e.g., a scout image). The target portion of the subject may be determined from the profile image, and the control device may control the couch 530 to move again, such that the target portion of the subject 532 may be located at the examination region of the field of view of the medical device 510 according to the determined target portion.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the medical system 500 may include a network and/or a terminal.

Figure 6:
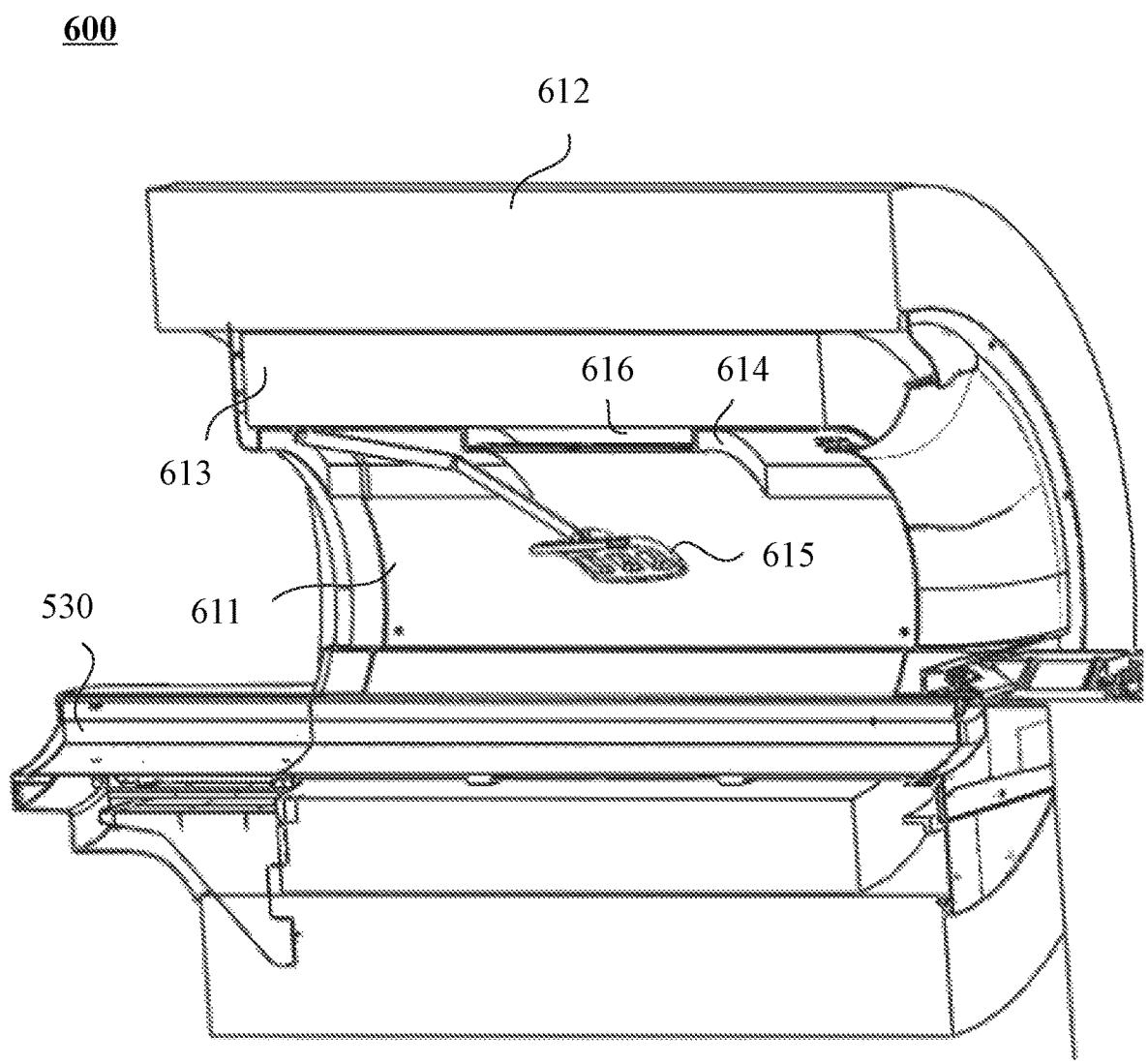
FIG. 6 is a schematic diagram illustrating a cross-sectional view of an exemplary medical device according to some embodiments of the present disclosure.

FIG. 6 is a schematic diagram illustrating a cross-sectional view of an exemplary medical device according to some embodiments of the present disclosure. As shown in FIG. 6, the medical device may include an MR scanner that includes a housing 611 (or gantry), one or more magnets 612, one or more gradient coils 613, and one or more volume coils 616 that are successively distributed from outside to inside. In some embodiments, the housing 611 may be cylindrical. It should be noted that the MR scanner is merely provided for the purposes of illustration, and not intended to limit the scope of the present disclosure In some embodiments, the housing 611 may include two end regions and a middle region. The end regions and/or the middle region may be provided with one or more accommodating cavities 614 configured to accommodate one or more receiving coils 615. The one or more receiving coils 615 may be configured to detect MR signals of the subject when the subject is scanned by the medical device 600. The cylinder wall of the housing 611 may be convex along the radial direction to form the one or more accommodating cavities 614. As used herein, an extension direction of the central long axis of the housing 611 may refer to an axial direction. The radial direction may be perpendicular to the extension direction of the central long axis and away from the central long axis. It should be understood that the shape and/or position of the one or more accommodating cavities 614 as shown in FIG. 6 is merely provided for the purposes of illustration, and not intended to limit the scope of the present disclosure.

The one or more receiving coils 615 may operatively be located in and/or out of the accommodating cavities 614. For example, one of the receiving coils 615 may be connected to the inside of one of the accommodating cavities 614 through a telescopic arm, and the receiving coils 615 may be flexible. After a couch (e.g., the couch 530) moves into the cavity of the medical device 600, a control device (e.g., the control device as described in FIG. 5) may control the telescopic arm to extend out of the one of the one or more accommodating cavities 614 so that the one of the one or more receiving coils 615 may be close to the body surface of the subject.

The one or more accommodating cavities 614 may be disposed on the housing 611 along the axial direction and/or the radial direction. For example, a plurality of different types of flexible coils such as a lower limb coil, an abdominal coil, a heart coil, a neck coil, etc., may be successively disposed along the radial direction. The plurality of different types of flexible coils may correspond to different portions (e.g., a lower limb, the abdomen, the heart, the neck, etc.) of the body of the subject. After identifying a target portion of a subject to be scanned, the control device may control the corresponding flexible coil to extend out of the one or more accommodating cavities 614 to close to the body surface of the subject. Accordingly, the one or more receiving coils may be automatically placed after the subject moves into the cavity according to the target portion of the subject, which may improve the efficiency of the MR scan. And the one or more receiving coils may be close to the subject to be scanned via one or more telescopic arms, which may improve the quality of MR signals received by the one or more receiving coils.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the medical device may include a console.

Figure 7:
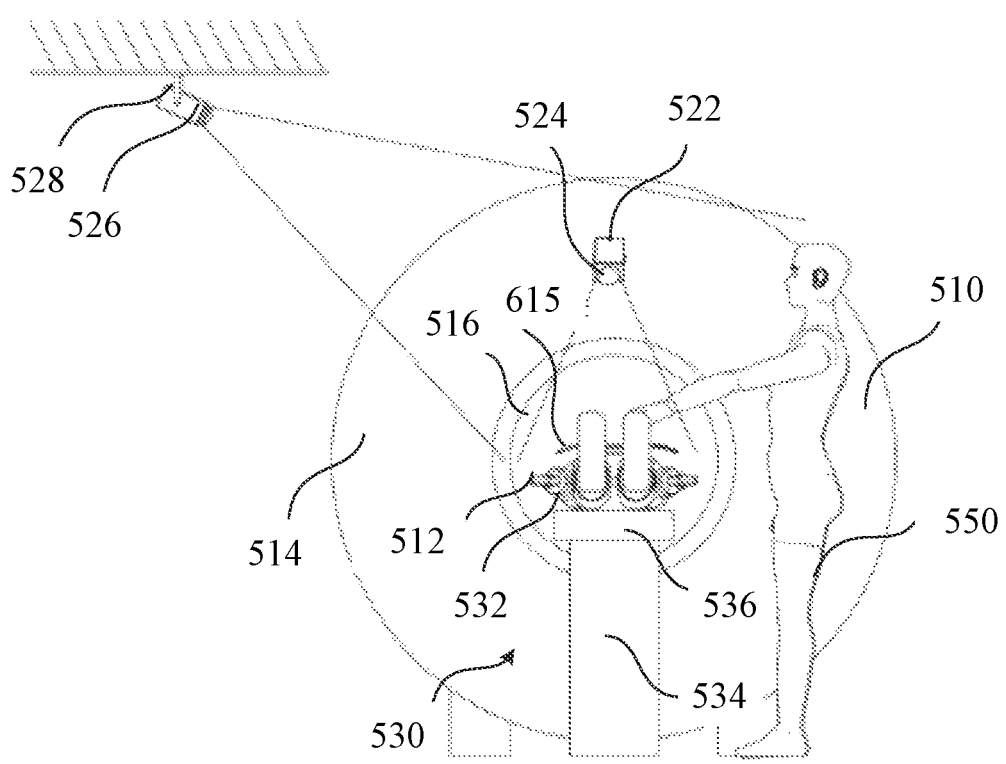
FIGS. 7-9 are schematic diagrams illustrating a process for positioning a subject in the medical system 500 according to some embodiments of the present disclosure.
Figure 8:
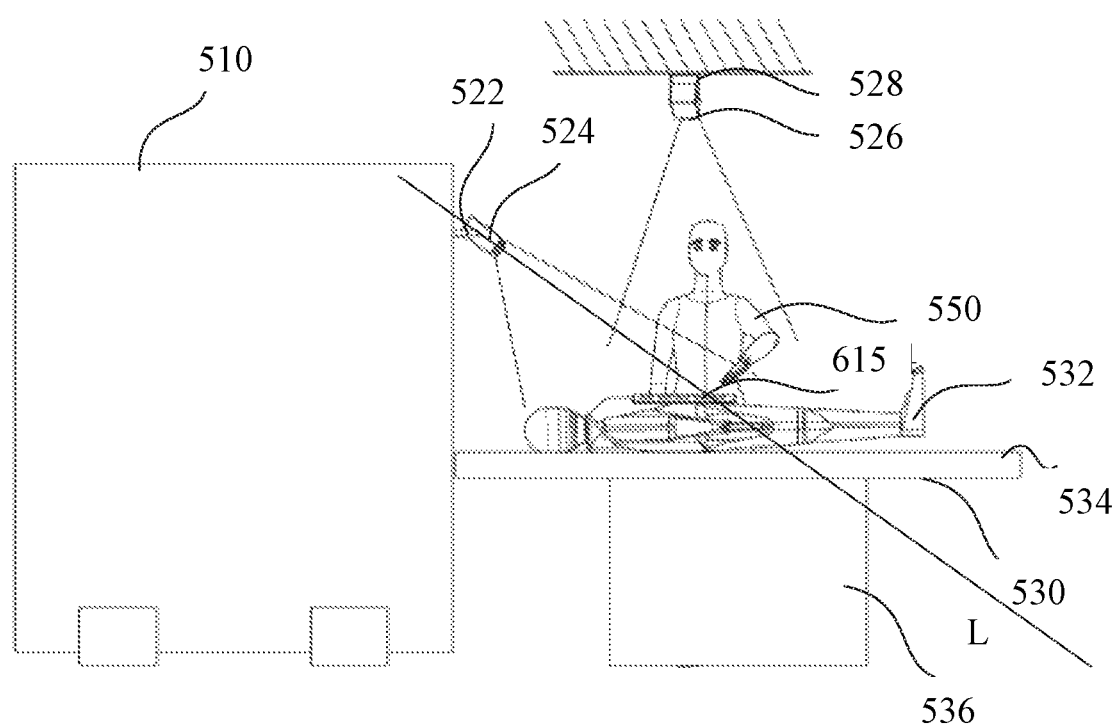
Figure 9:
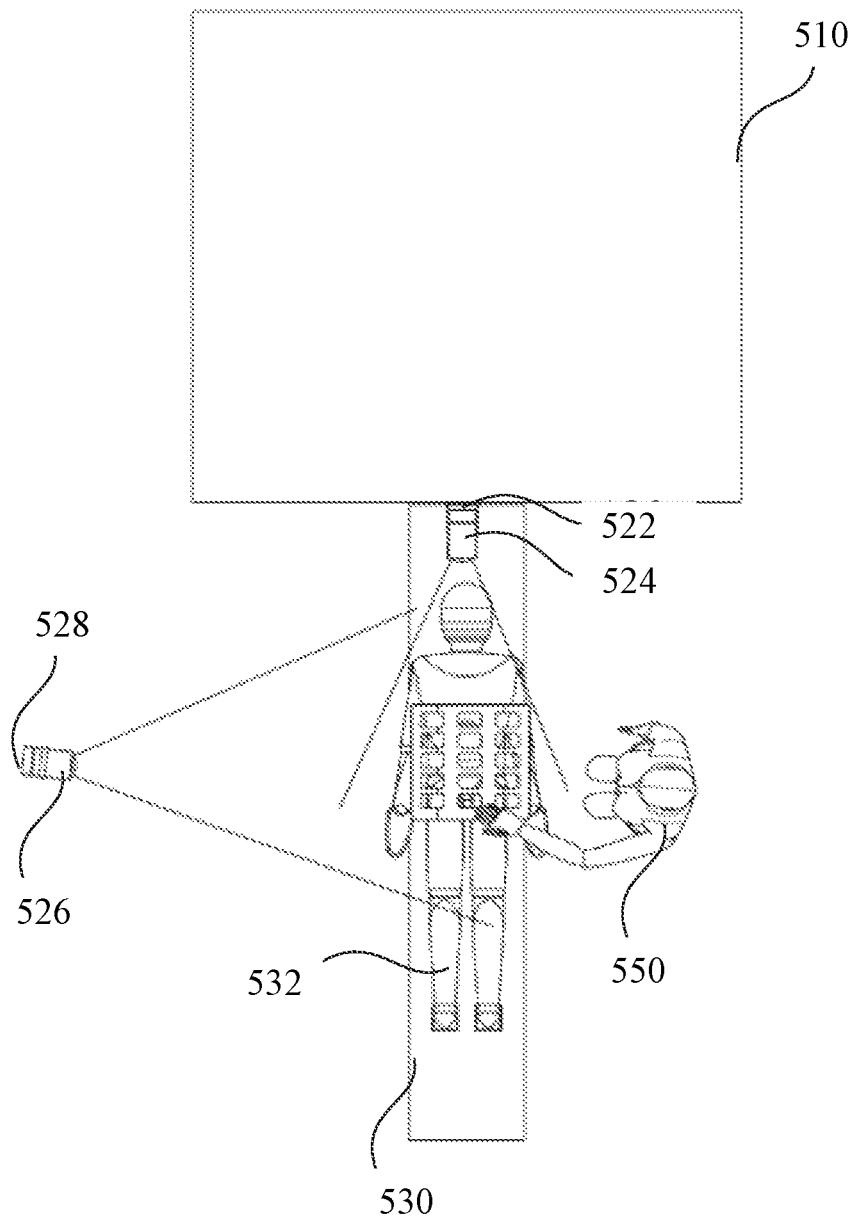

FIGS. 7-9 are schematic diagrams illustrating a process for positioning a subject in the medical system 500 according to some embodiments of the present disclosure.

As shown in FIGS. 7-9, when the target portion of the subject 532 needs to be scanned, the user 550 may make a specific action/gesture (e.g., "OK" gesture as shown in FIG. 11) at the target portion of the subject 532. The imaging devices 520 may acquire the posture information of the user 550, convert the posture information into an electrical signal, and transmit the electrical signal to the control device. The control device may identify the target portion of the subject 532 where the specific action/gesture is located and determine the position of the target portion of the subject 532. The target portion of the subject 532 may be moved to the examination region of the cavity 512 for scanning detection based on the position of the target portion.

For example, the control device may determine the distance between the target portion of the subject and an end of the couch 530. The control device may obtain the distance between the end of the couch 530 and the examination region of the cavity 512. The control device may further determine the distance between the target portion of the subject 532 and the examination region of the cavity 512 accordingly based on the distance between the target portion of the subject and the end of the couch 530 and the distance between the end of the couch 530 and the examination region of the cavity 512. Therefore, the control device may determine the moving distance of the couch 530 based on the distance between the target portion of the subject 532 and the examination region of the cavity 512.

In some embodiments, the control device may generate different control instructions according to different posture information of the user 550. The control device may control the operation of the couch 530 based on the control instructions. For example, the control device may control the couch 530 to move in different directions. The control device may also control the moving speed and distance of the couch 530. Therefore, the target portion of the subject 532 may reach the accurate position of the scanning region.

Figure 10:
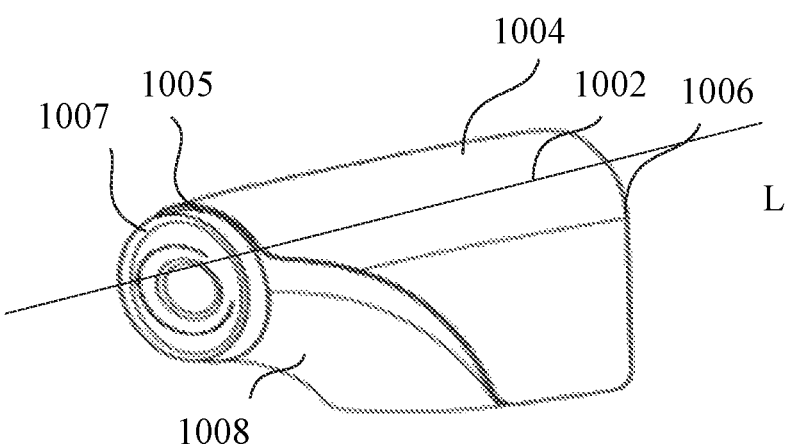
FIG. 10 is a schematic diagram illustrating an exemplary imaging device according to some embodiments of the present disclosure.

FIG. 10 is a schematic diagram illustrating an exemplary imaging device according to some embodiments of the present disclosure. As shown in FIG. 10, the imaging device 1000 may include a first end portion 1005 and a second end portion 1006 opposite to the first end portion 1005. The first end portion 1005 may face a couch (e.g., the couch 530 as described in FIG. 5), and the second end portion 1006 may face away from the couch 530. In some embodiments, the imaging device (e.g., the first imaging device 524) may include a magnetic shielding layer 1002 and a housing 1004. The magnetic shielding layer 1002 may be configured to shield the interference of external electromagnetic signals on the imaging device 1000. The magnetic shielding layer 1002 may at least partially enclose the housing 1004. The housing 1004 may include a cavity extending along the first end portion 1005 to the second end portion 1006. The extension line connecting the second end portion 1006 and the first end portion 1005 may intersect the surface where a couch plate of the couch (e.g., the couch plate 536) is located, which may ensure that the field of view of the imaging device 1000 (e.g., the first imaging device 524) covers the couch 530. The surface where the couch plate 536 is located may be a curved surface or a flat surface. The first end portion 1005 may be provided with a camera 1007, and the second end portion 1006 may be sealed. The camera 1007 may be movably disposed on the first end portion 1005. The camera 1007 may extend or retract the first end portion 1005. For example, the camera 1007 may come out from the cavity in response to the activation of the imaging device 1000. The camera 1007 may retract the cavity in response to the shutdown of the imaging device 1000.

In some embodiments, the first end portion 1005 may have an inclined surface 1008 inclined toward the second end portion 1006. The opposite ends of the inclined surface 1008 may have different distances from the second end portion 1006. The camera 1007 may be disposed on an end of the inclined surface 1008 relatively away from the second end portion 1006. In some embodiments, the inclined surface 1008 may have a certain curvature.

In some embodiments, the first end portion 1005 may be provided with a protective cover. In the non-working state, the protective cover may protect or shelter the camera 1007 to prevent the camera 1007 from collecting dust. When an operator (e.g., the user 550 as described in FIG. 5) enters the room where a medical device (e.g., the medical device 510 as described in FIG. 5) is placed, or when a sensing device (e.g., the one or more imaging devices 520 as described in FIG. 5) senses that the operator is close to the medical device, the protective cover may retract and the camera 1007 may be exposed, which may be convenient for collecting images.

In some embodiments, the camera 1007 may include a telephoto camera or a short-focus camera, and different lenses may be switched according to the distance of the operator or a subject (e.g., the subject 532) to be scanned or treated relative to the camera 1007, which may improve the resolution of the acquired image.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the camera 1007 may be one or more image sensors, such as a charged coupled device (CCD) or A complementary metal oxide semiconductor (CMOS) sensor.

FIGS. 11-14 are schematic diagrams illustrating exemplary gestures of an operator according to some embodiments of the present disclosure. As shown in FIG. 11, the gesture is an "OK" gesture. In some embodiments, the "OK" gesture may indicate an operation for confirmation. For example, with reference back to FIG. 5, the control device may control the couch 530 to start to move forward after an image of the user 550 representing the "OK" gesture is acquired by the first imaging device 524. As another example, the user 550 may make the "OK" gesture toward the target portion of the subject 532 and an image representing the "OK" gesture and the target portion of the subject 532 may be acquired by the second imaging device 526 or the first imaging device 524. The control device may determine the target portion of the subject 532 based on the "OK" gesture.

As shown in FIG. 12, the user 550 may extend the index finger or the thumb to indicate moving the couch 530 forward. Alternatively, as shown in FIG. 13, the user 550 may extend the arm or extend the palm with the thumb retracted to indicate moving the couch 530 forward.

In some embodiments, when the image acquired by the first imaging device 524 indicates that the user 550 extends the index finger and the thumb toward the direction opposite to the movement direction of the couch 530, the control device may control the couch 530 to move back.

In some embodiments, the user 550 may extend the arm toward the direction opposite to the movement direction of the couch 530 and extend the palm with the thumb retracted, which means that the couch 530 should be controlled to move back. After the first imaging device 524 acquires the image, the control device may control the couch 530 to move back.

As shown in FIG. 14, the gesture may be a "fist" gesture, which may indicate a pause of the couch 530. After the first imaging device 524 acquires the "fist" gesture, the control device may control the couch 530 to stop moving. In some embodiments, a gesture with the thumb retracted and the other finger extended may indicate a pause.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the gesture and the corresponding control instruction may be changed or set by a user.

Figure 15:
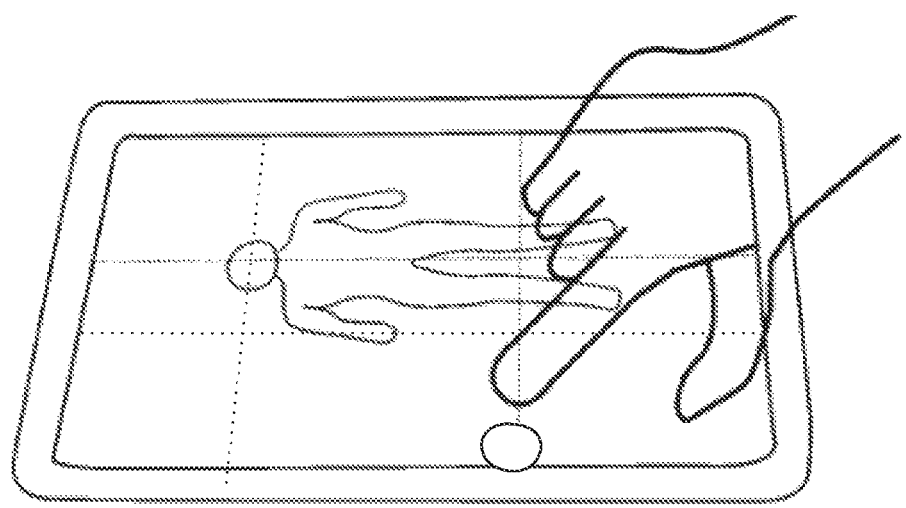
FIGS. 15-16 are schematic diagrams illustrating an exemplary process for determining a target portion of a subject via a terminal according to some embodiments of the present disclosure.
Figure 16:
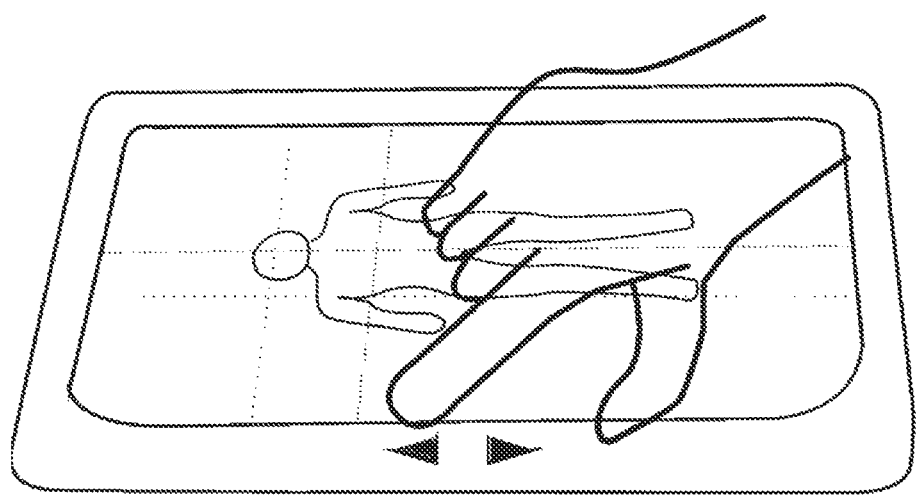

FIGS. 15-16 are schematic diagrams illustrating an exemplary process for determining a target portion of a subject via a terminal according to some embodiments of the present disclosure. The terminal may be configured to facilitate a communication between the operator (e.g., the user 550 as described in FIG. 5) and one or more components of a medical system (e.g., the medical system 500). In some embodiments, the terminal may be similar to or same as the terminal(s) 140 as described in FIG. 1. For example, the terminal may include an input component and/or an output component. Exemplary input components may include a keyboard, a mouse, a touch screen, a microphone, or the like, or a combination thereof. Exemplary output components may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

In some embodiments, the terminal may include a display. For example, with reference back to FIG. 5, the display may be located on a front panel of the medical device 510. When the couch plate 536 is controlled to move in the cavity 512, the control device may control the medical device 510 to acquire an overview image (e.g., a scout image) of the subject 532. According to the overview image, the approximate positions of different portions of the subject 532 (e.g., the torso, limbs, and various organs) may be determined. The terminal may be communicatively connected with the one or more imaging devices 520. The acquired overview image may be transmitted to the terminal and displayed on the terminal via the display. The user 550 may input the target portion of the subject 532 to be scanned via the terminal through the input component (e.g., a touch screen) or the display interface displaying the overview image.

In some embodiments, the user 550 may accurately input the target portion to be scanned to the terminal through the input component of the terminal (e.g., a touch screen (as shown in FIG. 15 and FIG. 16), buttons, knobs, a mouse, or keyboard). Taking a touch screen as an example, the overview image may be afforded an image coordinate system including an x-axis and a y-axis. One or more region positioning lines may be displayed on the terminal. For example, the region positioning lines may include two first lines distributed along the x-axis direction and two second lines distributed along the y-axis direction, and a region in the overview image representing the target portion to be scanned may be determined based on the one or more region positioning lines. For example, the user 550 may move or change the location of the region positioning lines by sliding a finger on the touch screen of the terminal to determine the region representing the target portion. Alternatively, the user 550 may describe an outline of the target portion by sliding a finger on the touch screen to determine an irregularly shaped region positioning line. A region enclosed by the irregularly shaped region positioning line may represent the target portion. In some embodiments, the touch screen may be mobile or fixed on the front panel of the medical device 510.

Figure 17:
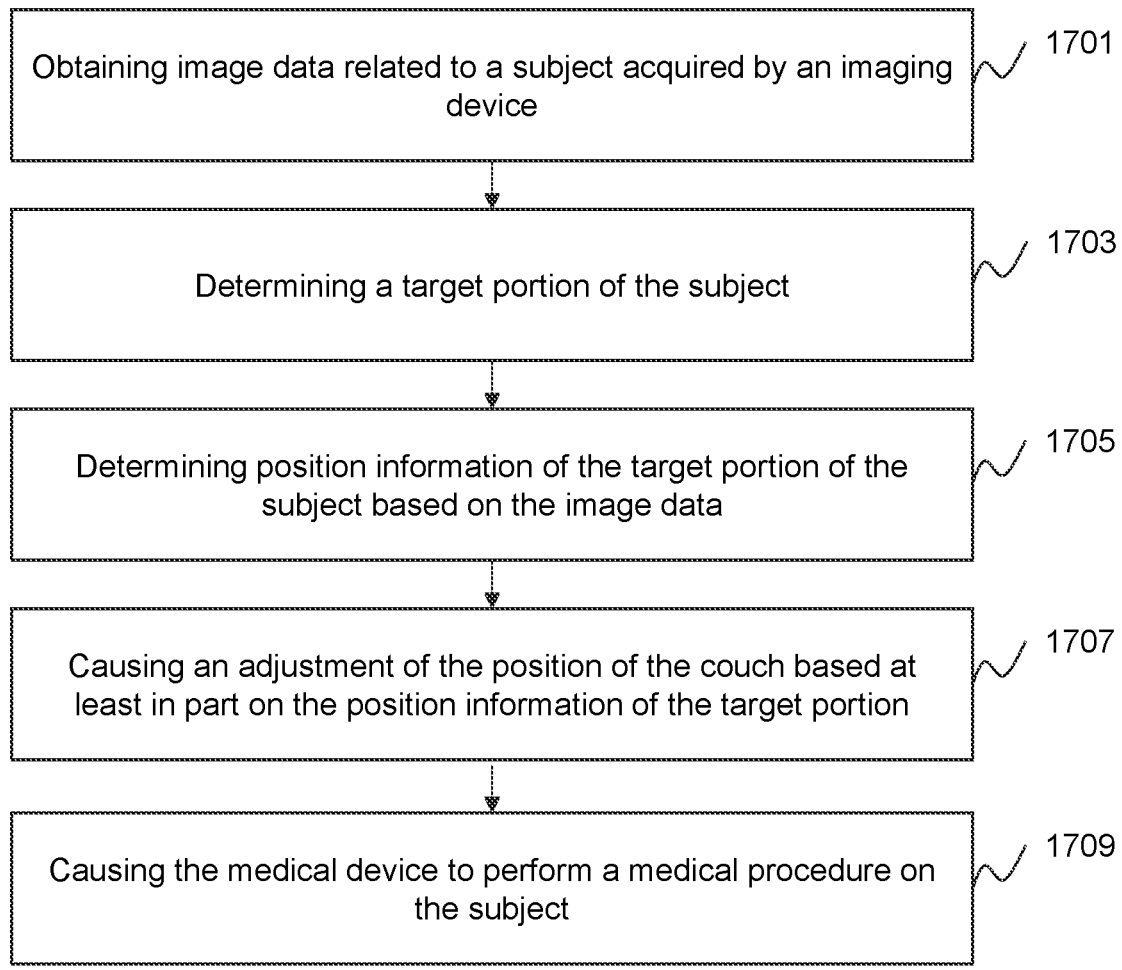
FIG. 17 is a flowchart illustrating an exemplary process for performing a medical procedure according to some embodiments of the present disclosure.

FIG. 17 is a flowchart illustrating an exemplary process for performing a medical procedure according to some embodiments of the present disclosure. In some embodiments, process 1700 may be implemented as a set of instructions (e.g., an application) stored in the storage device 150, storage 220, or storage 390. The processing device 130, the processor 210, and/or the CPU 340 may execute the set of instructions, and when executing the instructions, the processing device 130, the processor 210, and/or the CPU 340 may be configured to perform the process 1700. The operations of the illustrated process presented below are intended to be illustrative. In some embodiments, the process 1700 may be accomplished with one or more additional operations not described and/or without one or more of the operations discussed. Additionally, the order of the operations of process 1700 illustrated in FIG. 17 and described below is not intended to be limiting.

In 1701, the processing device 130 may obtain image data related to a subject acquired by an imaging device. The subject may be biological or non-biological as described elsewhere in the present disclosure. In some embodiments, the subject may include an operator of a medical device. In some embodiments, the subject may include a target portion that needs to be scanned or treated based on the medical device.

In some embodiments, the subject may be supported by a couch of a medical system as described elsewhere in the present disclosure (e.g., FIGS. 4-5 and the descriptions thereof). The image data of the subject may be acquired by the one or more imaging devices when the couch is at a position before the scan or treatment is performed. For example, the image data may be acquired when the target portion of the subject is located outside of the cavity of the medical device. In some embodiments, the medical device includes a magnetic resonance (MR) scanner. More descriptions regarding the medical device, the imaging devices, and/or the couch may be found elsewhere in the present disclosure. See, e.g., FIGS. 4-6.

In 1703, the processing device 130 may determine a target portion of the subject based on the image data. The target portion may be a portion of the subject to be scanned or treated by the medical device.

In some embodiments, the processing device 130 may determine the target portion by performing an object identification model (e.g., a trained machine learning model, an image segmentation model or algorithm, etc.).

In some embodiments, the processing device 130 may determine the target portion based on an input of an operator. More descriptions for determining the target portion based on the input of the operator may be found elsewhere in the present disclosure (e.g., FIGS. 15 and 16, and the descriptions thereof). For example, the operator may define a region from the image data by describing an outline of the target portion on the image data via an input device (e.g., a touch screen). The region may represent the target portion.

In some embodiments, a marker may be set on the location of the subject that corresponds to the target portion of the subject by an operator. The image data may include a representation of the marker indicating the target portion of the subject. The processing device 130 may identify the marker from the image data. The processing device 130 may determine the target portion based on the identified marker.

In some embodiments, the image data may include first posture information of a user indicating the target portion of the subject, the processing device 130 may identify the first posture information from the image data, and determine the target portion of the subject based on the first posture information of the user. For example, the image data may include the first posture information and the target portion of the subject. The first posture information may include an action of the operator pointing to the target portion of the subject. The processing device 130 may identify the first posture information from the image data using an object identification model and determine the target portion of the subject based on the identified posture information.

In some embodiments, the image data may include a first image of the subject acquired by one (e.g., the first imaging device 524 as shown in FIG. 5) of the one or more imaging devices and a second image including the first posture information of the user acquired by one (e.g., the second imaging device 526 as shown in FIG. 5) of the one or more imaging devices. A coordinate transform relationship between the first imaging device and the second imaging device may be obtained, or the two imaging devices may share a coordinate system or the coordinate systems of the two imaging devices may be orthogonal. In some embodiments, the first posture information of the operator (e.g., a gesture) corresponding to the target portion of the subject may be determined from the first image acquired by the first imaging device. According to the coordinate transform relationship between the first imaging device and the second imaging device, a location of the target portion of the subject in a coordinate system of the second imaging device may be determined based on a location of the first posture information in a coordinate system of the first imaging device. The processing device 130 may determine the target portion of the subject based on the location of the target portion of the subject in the coordinate system of the second imaging device.

In 1705, the processing device 130 may determine position information of the target portion of the subject based on the image data.

In some embodiments, the position information of the target portion of the subject may include a position of the target portion relative to an examination region (e.g., the center region of a scanning region) of the medical device or a position of the target portion relative to a reference position on the couch in a coordinate system of the medical device. In some embodiments, the position information may be denoted as a distance between the target portion and the examination region of the medical device or a distance between the target portion and the reference position on the couch in the coordinate system of the medical device. In some embodiments, the position of the target portion relative to the examination region may include the position of the target portion relative to the isocenter of the medical device.

In some embodiments, the processing device 130 may determine a position of the target portion relative to the reference position on the couch (e.g., an end of the couch) in a coordinate system associated with the image data (e.g., the coordinate system of the second imaging device or a coordinate system of the second image). The processing device 130 may determine the position of the target portion relative to the reference position on the couch based on the position of the target portion relative to the reference position on the couch (e.g., an end of the couch) in the coordinate system associated with the image data and a coordinate transform relationship between the coordinate system associated with the image data and the coordinate system of the medical device. In some embodiments, the processing device 130 may determine the position of the target portion relative to the examination region of the medical device based on the position of the target portion relative to the reference position on the couch and a position of the reference position on the couch relative to the examination region of the medical device.

In 1707, the processing device 130 may cause an adjustment of the position of the couch based at least in part on the position information of the target portion. The adjusted position of the couch may be such that the target portion of the subject is located at an examination region of the cavity of the medical device. In some embodiments, the processing device 130 may determine the distance between the target portion and the examination region of the medical device based on the distance between the target portion and the reference position on the couch and a distance between the reference position on the couch and the examination region of the medical device. The processing device 130 may designate the distance between the target portion and the examination region of the medical device as a movement distance of the couch. The processing device 130 may cause the couch to move toward the cavity of the medical device with the determined movement distance.

In some embodiments, the image data may include second posture information of a user acquired by one of the one or more imaging devices. The second posture information may indicate an operation of the user for controlling a movement of the couch. The processing device 130 may determine a type of operation of the user for controlling the movement of the couch. In some embodiments, the operation of the user for controlling the movement of the couch may include a specific action/gesture made by the operator. The type of operation may include a moving forward operation, a moving backward operation, a stop operation, or the like. For example, the operation may be a moving forward operation, and the processing device 130 may cause the couch to move forward. As another example, the operation may be a stop operation, and the processing device 130 may cause the couch to stop moving. In some embodiments, the processing device 130 may determine a movement distance of the couch based on the position information of the target portion of the subject. Then the processing device 130 may cause the couch to move the moving distance based on the type of operation of the user for controlling the movement of the couch.

In 1709, the processing device 130 may cause the medical device to perform a medical procedure on the subject. After the target portion of the subject is located at an examination region of the cavity of the medical device, the medical device may perform a medical procedure on the subject. The adjustment process may be completed automatically, which is more convenient and faster.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 1703 and operation 1705 may be combined into one operation including determining the position information of the subject. As another example, one or more other optional operations (e.g., a storing operation) may be added elsewhere in the process 1700.

Figure 18:
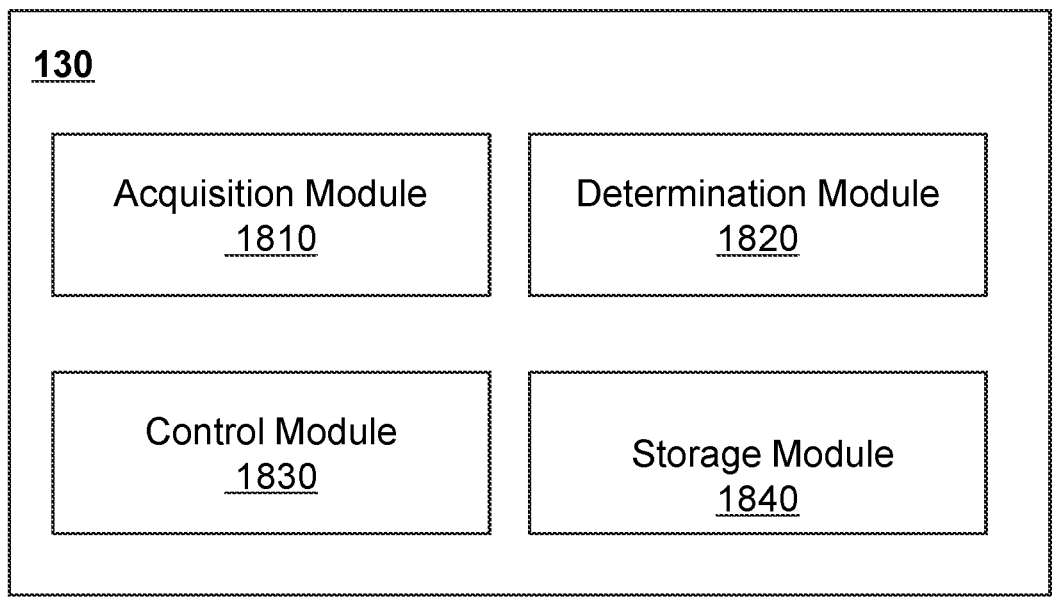
FIG. 18 is a block diagram illustrating an exemplary processing device according to some embodiments of the present disclosure.

FIG. 18 is a block diagram illustrating an exemplary processing device according to some embodiments of the present disclosure. In some embodiments, processing device 130 may be implemented on a computing device 200 (e.g., the processor 210) illustrated in FIG. 2 or a CPU 340 as illustrated in FIG. 3. As illustrated in FIG. 18, the processing device 130 may include an acquisition module 1810, a determination module 1820, a control module 1830, and a storage module 1840. Each of the modules described above may be a hardware circuit that is designed to perform certain actions, e.g., according to a set of instructions stored in one or more storage media, and/or any combination of the hardware circuit and the one or more storage media.

The acquisition module 1810 may be configured to obtain data (e.g., image data, models, etc.) used in a medical procedure. For example, the acquisition module 1810 may obtain image data related to a subject acquired by an imaging device. The subject may be biological or non-biological as described elsewhere in the present disclosure. In some embodiments, the subject may include an operator of a medical device. In some embodiments, the subject may include a target portion that needs to be scanned or treated based on the medical device. In some embodiments, the subject may be supported by a couch of a medical system as described elsewhere in the present disclosure (e.g., FIGS. 4-5 and the descriptions thereof). The image data of the subject may be acquired by the one or more imaging devices when the couch is at a position before the scan or treatment is performed. For example, the image data may be acquired when the target portion of the subject is located at outside of the cavity of the medical device. In some embodiments, the medical device includes a magnetic resonance (MR) scanner. More descriptions regarding the medical device, the imaging devices, and/or the couch may be found elsewhere in the present disclosure. See, e.g., FIGS. 4-6. As another example, the acquisition module 1810 may obtain an object identification model (e.g., a trained machine learning model, an image segmentation model or algorithm, etc.).

The determination module 1820 may be configured to determine a target portion of the subject based on the image data. The target portion may be a portion of the subject to be scanned or treated by the medical device. In some embodiments, the determination module 1820 may determine the target portion by performing the object identification model (e.g., a trained machine learning model, an image segmentation model or algorithm, etc.). In some embodiments, the determination module 1820 may determine the target portion based on information related to the image data. The information related to the image data may include an input of an operator, a marker set by an operator, or first posture information of a user, each of which may indicate the target portion of the subject. The determination module 1820 may identify the information related to the image data using an object identification model and determine the target portion of the subject based on the identified information. In some embodiments, the image data may include a first image of the subject acquired by one (e.g., the first imaging device 524 as shown in FIG. 5) of the one or more imaging devices and a second image including the first posture information of the user acquired by one (e.g., the second imaging device 526 as shown in FIG. 5) of the one or more imaging devices. In some embodiments, the first posture information of the operator (e.g., a gesture) corresponding to the target portion of the subject may be determined from the first image acquired by the first imaging device. According to a coordinate transform relationship between the first imaging device and the second imaging device, a location of the target portion of the subject in a coordinate system of the second imaging device may be determined based on a location of the first posture information in a coordinate system of the first imaging device. The determination module 1820 may determine the target portion of the subject based on the location of the target portion of the subject in the coordinate system of the second imaging device.

The determination module 1820 may further be configured to determine position information of the target portion of the subject based on the image data. The position information of the target portion of the subject may include a position of the target portion relative to the examination region of the medical device or a position of the target portion relative to a reference position on the couch in a coordinate system of the medical device. In some embodiments, the position information may be denoted as a distance between the target portion and the examination region of the medical device or a distance between the target portion and the reference position on the couch in the coordinate system of the medical device.

The control module 1830 may be configured to cause an adjustment of the position of the couch based at least in part on the position information of the target portion. The adjusted position of the couch may be such that the target portion of the subject is located at an examination region of the cavity of the medical device. In some embodiments, the control module 1830 may determine the distance between the target portion and the examination region of the medical device based on the distance between the target portion and the reference position on the couch and a distance between the reference position on the couch and the examination region of the medical device. The distance between the target portion and the examination region of the medical device may be designated as a movement distance of the couch. The control module 1830 may cause the couch to move toward the cavity of the medical device with the determined movement distance. In some embodiments, the image data may include second posture information of a user acquired by one of the one or more imaging devices. The second posture information may indicate an operation of the user for controlling a movement of the couch. The control module 1830 may control the movement of the couch based on a type of the operation. In some embodiments, the operation for controlling the movement of the couch may include a specific action/gesture made by the operator. The type of the operation may include a moving operation, a stop operation, or the like.

The storage module 1840 may be configured to store data and/or instructions associated with the medical system 100. For example, the storage module 1840 may store image data, one or more machine learning models, etc. In some embodiments, the storage module 1840 may be the same as the storage device 150 in configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
a medical device including a cavity;
a couch configured to support a subject;
one or more imaging devices configured to acquire image data, the image data indicating at least one of a target portion of the subject and posture information of a user, and the target portion being identified from the image data based on the posture information of the user; and
a control device configured to:
control a movement of the couch based on at least one of position information of the target portion of the subject and the posture information of the user; and
control receiving coils to extend out based on the posture information of the user.

2. The system of claim 1, wherein the one of the one or more imaging devices includes a first end facing the couch and a second end facing away from the couch, an extension line connecting the second end with the first end intersecting a surface where a couch plate of the couch is located.

3. The system of claim 1, wherein the one of the one or more imaging devices includes a magnetic shielding layer and a housing, the magnetic shielding layer at least in part enclosing the housing, the housing including a housing cavity extending from a first end to a second end, the one of the one or more imaging devices including at least one of an infrared sensor, a camera, and a video camera that is located at the first end, the second end being sealed.

4. The system of claim 3, wherein the camera includes a telephoto camera or a short-focus camera.

5. The system of claim 1, wherein the one or more imaging devices includes a first imaging device configured to acquire a first image including a representation of the target portion of the subject.

6. The system of claim 5, wherein the one or more imaging devices includes a second imaging device configured to acquire a second image including the posture information of the user.

7. The system of claim 2, wherein an angle between the extension line connecting the second end with the first end and the surface is within a range of 5 degrees to 80 degrees.

8. The system of claim 1, wherein the medical device includes a magnetic resonance imaging (MRI) device, and the control device is disposed in the MRI device.

9. A system, comprising:
at least one storage medium including a set of instructions; and
at least one processor in communication with the at least one storage medium, wherein when executing the set of instructions, the at least one processor is directed to cause the system to:
obtain image data related to a subject on a couch that is acquired by at least two imaging devices when the couch is located outside a cavity of a medical device, the image data indicating at least one of a target portion of the subject and posture information of a user;
identify the target portion from the image data based on the posture information of the user, wherein the at least one processor is directed to cause the system to:
obtain a coordinate transform relationship between the at least two imaging devices; and
determine, based on the posture information of the user and the coordinate transform relationship, the target portion;
determine, based on the image data, position information of the target portion of the subject;
cause, based at least in part on the position information of the subject, an adjustment of a position of the couch, an adjusted position of the couch being such that the subject is moved into the cavity of the medical device.

10. The system of claim 9, wherein the image data includes a representation of a marker indicating the subject, and to determine the position information of the subject, the at least one processor is directed to cause the system to:
identify the marker from the image data.

11. The system of claim 9, wherein the image data includes the posture information of the user indicating the position information of the subject, and to determine the position information of the target portion of the subject in the image data, the at least one processor is directed to cause the system to:
identify the posture information from the image data; and
determine the position information of the target portion of the subject based on the posture information of the user, wherein the position information of the target portion of the subject includes a position of the target portion relative to an examination region of the medical device or a position of the target portion relative to a reference position on the couch in a coordinate system of the medical device.

12. The system of claim 9, wherein the image data includes a first image of the subject acquired by one of the at least two imaging devices and a second image including first posture information of the user acquired by one of the at least two imaging devices.

13. The system of claim 9, wherein the medical device includes a magnetic resonance (MR) scanner, wherein the at least one processor is further configured to cause the couch to an examination region of the MR scanner.

14. An MR system, comprising:
an MR device including a main field magnet having an examination region;
a couch including a support portion and a couch plate supported by the support portion, the support portion being in communication with the MR device, the couch plate, adapted to receive a subject, being moveable relative to the support portion;
one or more imaging devices configured to acquire image data, the image data indicating posture information of a user; and
a control device configured to:
determine a position of a target portion in a coordinate system associated with the image data;
obtain a coordinate transform relationship between the coordinate system associated with the image data and a coordinate system of a medical device;
determine a position of the target portion in the coordinate system of the medical device based on the position of the target portion in the coordinate system associated with the image data and the coordinate transform relationship;

control, based on the position of the target portion in the coordinate system of the medical device, a movement of the couch plate.

15. The system of claim 14, wherein the one of the one or more imaging devices includes a first end facing the couch and a second end facing away from the couch, an extension line connecting the second end with the first end intersecting a surface where the couch plate of the couch is located.

16. The system of claim 15, wherein the one of the one or more imaging devices includes a magnetic shielding layer and a housing, the magnetic shielding layer at least in part enclosing the housing, the housing including a housing cavity extending from the first end to the second end, the one of the one or more imaging devices including at least one of an infrared sensor, a camera, and a video camera that is located at the first end, the second end being sealed.

17. The system of claim 15, wherein an angle between the extension line connecting the second end with the first end and the surface is within a range of 5 degrees to 80 degrees.

18. The system of claim 1, wherein the receiving coils are flexible coils, a plurality of different types of the flexible coils correspond to different portions of a body of the subject; and the control device is further configured to:
control the corresponding flexible coil to extend out to close to a body surface of the subject after identifying the target portion of the subject to be scanned.

19. The system of claim 9, wherein the at least one processor is further directed to cause the system to:
determine a location of the target portion of the subject with respect to a reference location represented in the image data of the subject;
determine a distance between the reference location and an examination region of the cavity; and
determine a distance the couch needs to move based on the distance between the reference location and the examination region of the cavity and the location of the target portion of the subject with respect to the reference location.

20. The system of claim 14, wherein the medical device includes one or more accommodating cavities configured to accommodate one or more receiving coils, the receiving coils are capable of extending out of the one or more accommodating cavities based on the posture information of the user.

* * * * *